United States Patent [19]
Michielli et al.

[11] Patent Number: 5,549,705
[45] Date of Patent: Aug. 27, 1996

[54] PROSTHESIS WITH INTEGRAL PROXIMAL SPACER

[75] Inventors: Michael Michielli, Hoboken; Glen Kashuba, River Edge; J. Mel Goldenberg, Upper Saddle River; Jon I. Klippel, Basking Ridge, all of N.J.

[73] Assignee: Howmedica, Inc., Rutherford, N.J.

[21] Appl. No.: 402,443

[22] Filed: Mar. 13, 1995

Related U.S. Application Data

[62] Division of Ser. No. 234,485, Apr. 28, 1994, Pat. No. 5,507,832.

[51] Int. Cl.$^6$ .................................. A61F 2/32; A61F 2/30
[52] U.S. Cl. ........................................................ 623/23
[58] Field of Search ............................. 623/16, 18, 20, 623/22, 23; 606/86, 79, 80

[56] References Cited

U.S. PATENT DOCUMENTS

| | | | |
|---|---|---|---|
| 4,038,703 | 8/1977 | Bokros | 623/23 |
| 4,718,916 | 1/1988 | Morscher | 623/23 |
| 4,728,335 | 3/1988 | Jurgutis | 623/23 |
| 4,753,657 | 6/1988 | Lee et al. | 623/23 |
| 4,790,852 | 12/1988 | Noiles | 623/23 |
| 4,842,606 | 6/1989 | Kranz et al. | 623/23 |
| 5,007,931 | 4/1991 | Smith | 623/23 |
| 5,018,285 | 5/1991 | Zolman et al. | 623/23 |

FOREIGN PATENT DOCUMENTS

| | | | |
|---|---|---|---|
| 466638 | 1/1992 | European Pat. Off. | 623/23 |
| 2668058 | 4/1992 | France | 623/23 |
| 4125152 | 2/1993 | Germany | 623/23 |
| 2142830 | 1/1985 | United Kingdom | 623/23 |

*Primary Examiner*—David Isabella
*Attorney, Agent, or Firm*—Pennie & Edmonds

[57] ABSTRACT

A prosthesis with an integral proximal spacer is described. The prosthesis has a base element with a textured surface to aid in adhesion to bone cement. The integral spacer has a generally tripod shape. A top circumferential portion at least partially surrounds the proximal end of the prosthesis, and three legs extend distally along the length of the prosthesis. Also disclosed is the process for making the prosthesis and spacer, which preferably involves injection molding of PMMA.

5 Claims, 6 Drawing Sheets

PROSTHESIS WITH INTEGRAL PROXIMAL SPACER

This is a division, of application Ser. No. 08/234,485 filed Apr. 28, 1994 now U.S. Pat. No. 5,507,832.

BACKGROUND OF THE INVENTION

The present invention relates to orthopaedic implants in general, and more particularly to a prosthesis used in conjunction with a proximal spacer.

In orthopaedic implantation surgery, an enlarged canal is created through the reaming of a bone canal and removal of bone tissue. Bone cement is then inserted into the canal. The implant must be quickly inserted into the canal with the proper alignment, before the bone cement cures. It is desirable to provide a prosthesis that can be easily implanted in the correct position and will form a strong bond within a bone canal with the supplied bone cement.

It is known to provide implants with a coating of material to help bonding with bone cement in a bone canal. For example, in U.S. Pat. No. 4,283,799 to Pratt, Jr. et al., a pre-coated hip prosthesis is disclosed. All or most of the surface of the prosthesis is covered with a material that is bonded to the prosthesis. Similarly, U.S. Pat. No. 4,491,987 to Park discloses a prosthesis with a uniform polymer coating on substantially the entire surface of the prosthesis. In addition, U.S. Pat. Nos. 4,281,420 and 4,336,618 to Raab provide a prosthesis coated with a polymethylmethacrylate (PMMA) film fixedly adhered to the surface. The film is applied to the prosthetic surface after treating, and then the film is annealed. Similarly, U.S. Pat. No. 4,365,359 to Raab utilizes a silane coupling agent to adhere the PMMA film to a prosthetic element and further enhance the adherence of the prosthesis. A coating of bone cement compatible polymer around the proximal portion of a prosthesis is disclosed in U.S. Pat. No. 4,881,536 to Noble et al. However, the solid coating incorporates stresses through the design, creating a tendency of cracking or disattachment.

Another technique to increase the ability of the prosthesis to adhere to the bone cement is the use of a textured surface on the prosthesis. An example of such a surface is shown in U.S. Pat. No. 4,795,472 to Crowninshield et al.

While the pre-coats and textured surfaces described above may help a prosthesis better adhere to the bone cement and bone, they do not provide other useful features. Such features include pressurizing the bone cement as the prosthesis is inserted and aligning the prosthesis centrally within the bone canal.

Separate spacers for centralizing the prosthesis in the bone canal are disclosed in the art, for example in U.S. Pat. No. 4,827,919 to Barbarito et al. In use, such spacers are placed over the proximal opening of the bone canal either immediately before or after the bone cement is injected into the canal. The prosthesis is then inserted through the spacer into the canal. Such spacers have the disadvantage that, as the prosthesis is inserted, the bone cement is forced out of the canal and obscures the surgeon's view of the spacer, such that it is difficult to determine whether the prosthesis is properly seated.

SUMMARY OF THE INVENTION

An object of the invention is to provide a novel prosthesis with an integral proximal spacer that allows for more effective adherence and improved accuracy of placement of the prosthesis in a patient and to allow easier manufacture of the prosthesis.

An additional object of the invention is to provide a prosthesis with an integral proximal spacer that allows for improved pressurizing and aligning of the prosthesis within the bone cement in a bone canal. The prosthesis of the present invention is specifically directed to use in hip replacement surgery, with the prosthesis consisting of a hip femoral component that is inserted into the femur of a patient after removing the top portion and a central area of the femur. It is understood, however, that the prosthesis of the present invention could be adapted for use in other orthopaedic surgery, such as knee surgery.

These and other objects are achieved according to the present invention by a combined prosthesis and integral, proximal spacer preferably made of a bone cement material molded onto the prosthesis. The spacer is shaped to pressurize the bone cement within the enlarged canal upon insertion, and to align the prosthesis centrally within the canal. Preferably the spacer is molded directly onto the prosthesis as it is formed. In order to ensure a secure bond between the spacer and prosthesis shaft, a textured surface is provided on the prosthesis. For further bonding improvement, a series of dimples can be provided on the surface of the prosthesis. Also, a textured surface may be provided on the prosthesis shaft adjacent the spacer for increased adherence to bone cement in the canal.

The prosthesis and integral bone cement spacer according to the present invention are preferably made by an injection molding process. The process includes the use of high pressure injection molding, using powdered PMMA under heat and pressure to form the spacer around the prosthesis.

To prepare for the molding process, the prosthesis first undergoes a gas plasma cleaning process that prepares the prosthesis for receiving bone cement. An energized oxygen and argon gas mixture removes any surface oils from the prosthesis. The process provides a super clean surface for the prosthesis which is an active/wettable surface. The prosthesis is preheated before placing in the mold and forming the spacer using high pressure injection molding.

DETAILED DESCRIPTION

Figure 1:
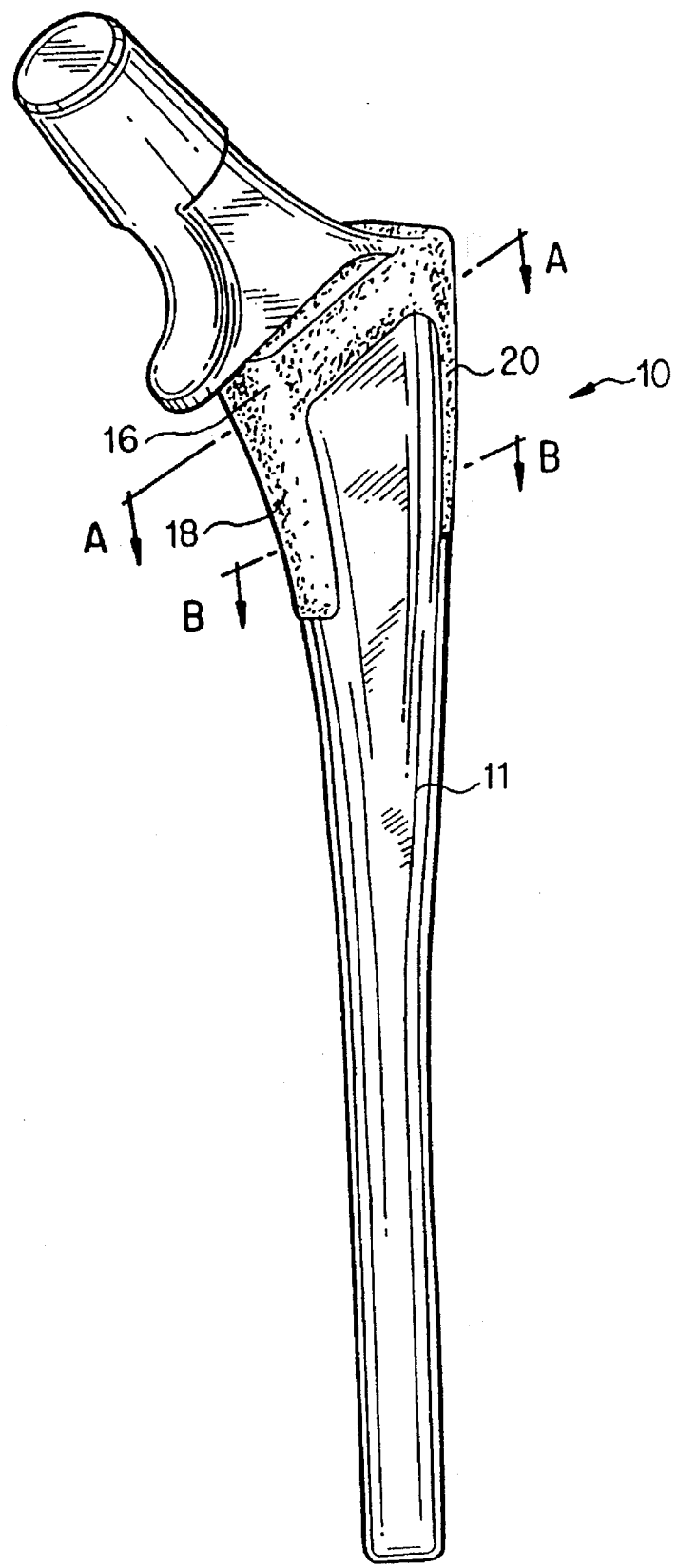
FIG. 1 is a perspective view of a prosthesis according to the invention illustrating the base element and integral spacer.

FIG. 1 illustrates a femoral prosthesis 10 comprising a prosthesis base element or shaft 11 with an integral proximal spacer 12 according to the present invention. The general shape of a femoral prosthesis is known and disclosed, for example, in U.S. Pat. No. 4,881,536 to Noble et al, which is incorporated herein by reference. The prosthesis base element is preferably constructed of a titanium alloy.

Figure 2:
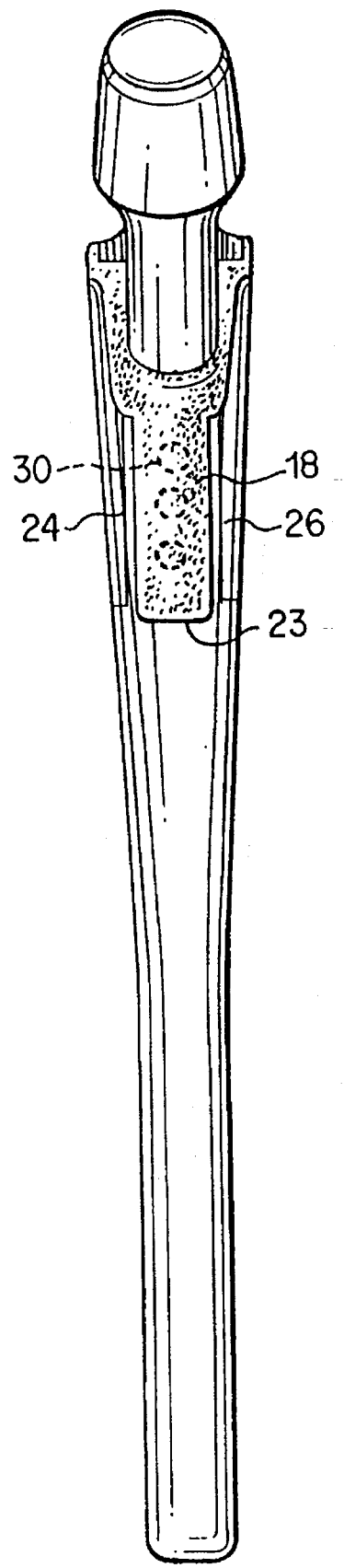
FIG. 2 is an medial view of the prosthesis of FIG. 1.
Figure 3:
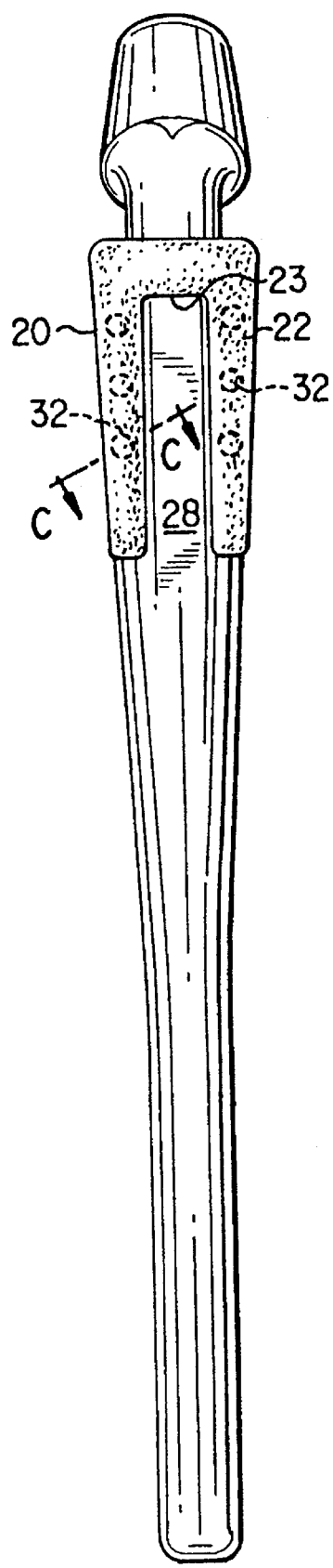
FIG. 3 is an lateral view of the prosthesis of FIG. 1.
Figure 4:
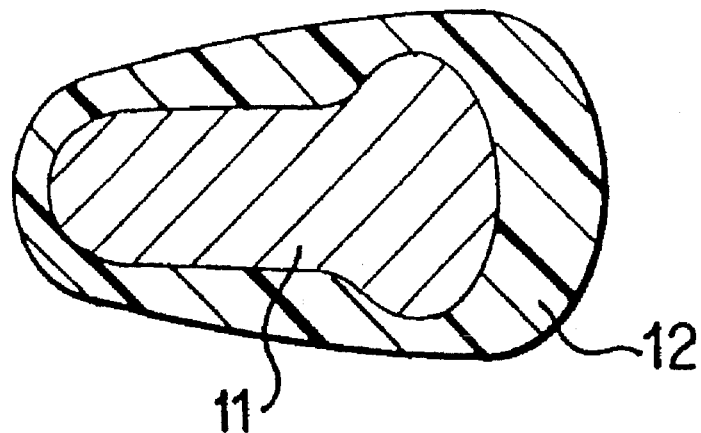
FIG. 4 is a cross-sectional view of the prosthesis through line A—A of FIG. 1.
Figure 5:
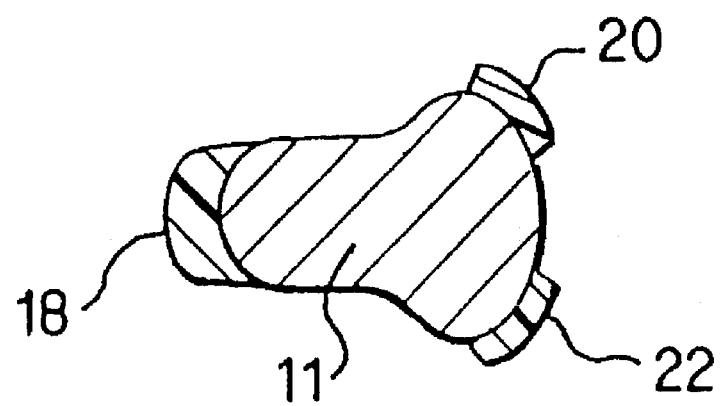
FIG. 5 is a cross-sectional view of the prosthesis trough line B—B of FIG. 1.

Spacer 12 is illustrated in FIG. 1 as it appears affixed to the base element 11. The spacer has a circumferential portion 16 and, in this embodiment, three distally extending legs 18, 20, and 22. First leg 18 extends distally along the medial face of the prosthesis 10, as best shown in FIG. 2. The second leg 20 and third leg 22 extend distally along the lateral-anterior and lateral-posterior corners, as shown in FIG. 3. The legs preferably range in length from 0.600" to 1.125". Legs 18, 20, and 22 have a gradually tapering shape ending in a feathered edge 23, which blends smoothly against the prosthesis substantially without discontinuity so as to create a surface that is inserted into a bone canal with little resistance and without catching on the edge of the canal. The tapering is preferably approximately five degrees. Spacer 12 generally aids the surgeon in the correct alignment of the prosthesis within the bone canal, as the tapered legs 18, 20, and 22 allow for a gliding insertion, and the circumferential portion 16 assures final positioning. The cross-sectional views are shown in FIGS. 4 and 5.

Figure 11:
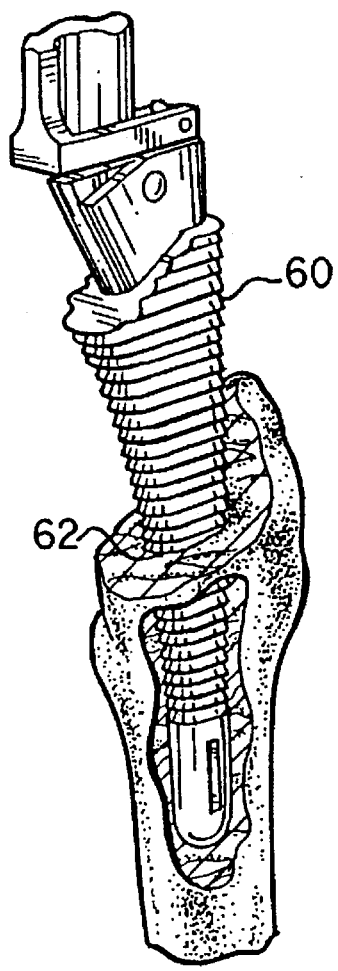
FIG. 11 is a perspective view of a bone canal reamer sizing the femoral canal for insertion of the prosthesis of the invention.

To ensure correct alignment, the canal is preferably prepared, as shown in FIG. 11, with a bone canal reamer 60 matched to the size of the prosthesis and integral spacer. The reamer 60 and spacer are match-sized so as to create substantially sealing contact between the circumferential portion 16 of the spacer and the bone canal opening 62. With the canal properly sized to match the spacer, circumferential portion 16 acts to pressurize the bone cement during the final insertion of the prosthesis and spacer into a bone canal.

Spacer 12 thus ensures neutral alignment of the prosthesis in the bone canal and the circumferential portion 16 helps to pressurize the bone cement within the canal. Excessive pressurization, however, is to be avoided to prevent bone plug "blowout" and difficulty in final implant seating. This problem is prevented in the present invention by the provision of the separate legs, preferably three legs 18, 20, and 22, which create spaces for cement "venting" as the prosthesis is introduced into the bone canal. This also allows for the newly introduced cement to disperse evenly. Final pressurization occurs only when circumferential portion 16 enters the canal and prevents further venting of cement. The spacer's tripod shape also allows for simple molding manufacture, and allows for reduced stresses to be present in the final molded article.

The unique shape of the bone cement spacer 12 provides other advantages to the surgeon. The "tripod" structure of relatively narrow circumferential portion 16 and three extending legs 18, 20, and 22 provides relief zones 24, 26, and 28 between the molded arms of the geometry, allowing for material shrink during the cooling cycle following molding. The circumferential portion is approximately 0.250" wide in the preferred embodiment, and the legs are approximately 0.300" to 0.500" (13 mm) wide. The relief zone between the two lateral projections is approximately 0.200" to 0.300" wide. The provision of such relief zones prevents the incorporation of excessive stresses, which could result in cracking and/or disattachment. The spacer is preferably constructed of polymethylmethacrylate (PMMA).

The prosthesis 10 is provided with two areas of texture 14, one on the anterior side and one on the posterior side of base element 11. These areas are not covered by spacer 12. The textured 14 areas are designed to provide very strong bonding at the locations where the prosthesis will be under large amounts of torque rotation and stress between the prosthesis and bone cement. The texture can be in the form of a waffled macro-texture as shown 14, or vertical grooves. The remaining surface of base element 11 has a slightly rough texture as is known n the art (such as formed by grit blasting).

Figure 8:
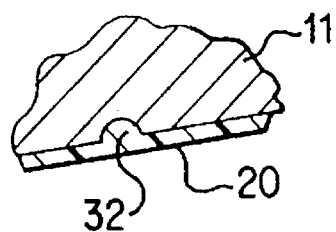
FIG. 8 is an enlarged cross-sectional view through line C—C in FIG. 3, showing a typical interlocking dimple.

The prosthesis is further preferably provided with a mechanical interlock between the spacer and base element. Base element 11 has a plurality of dimples, or concave hemispheres, located on the surface of the base element on the lateral and medial sides under the spacer. Referring to FIGS. 2 and 3, most preferably, there are three dimples 30 on the medial side, and six (two rows of three) dimples 32 on the lateral side. A cross-section of a typical dimple is illustrated in FIG. 8. A mechanical interlock is formed when the spacer is molded around the base element and flows into the dimples. The interlock is strengthened by the shrink properties of the PMMA material used for the spacer as the PMMA cures onto the prosthesis. The key attributes of the dimples which maximize interlock are the location of the dimples, their depth, radius and angulation with respect to the stem surface.

Figure 6:
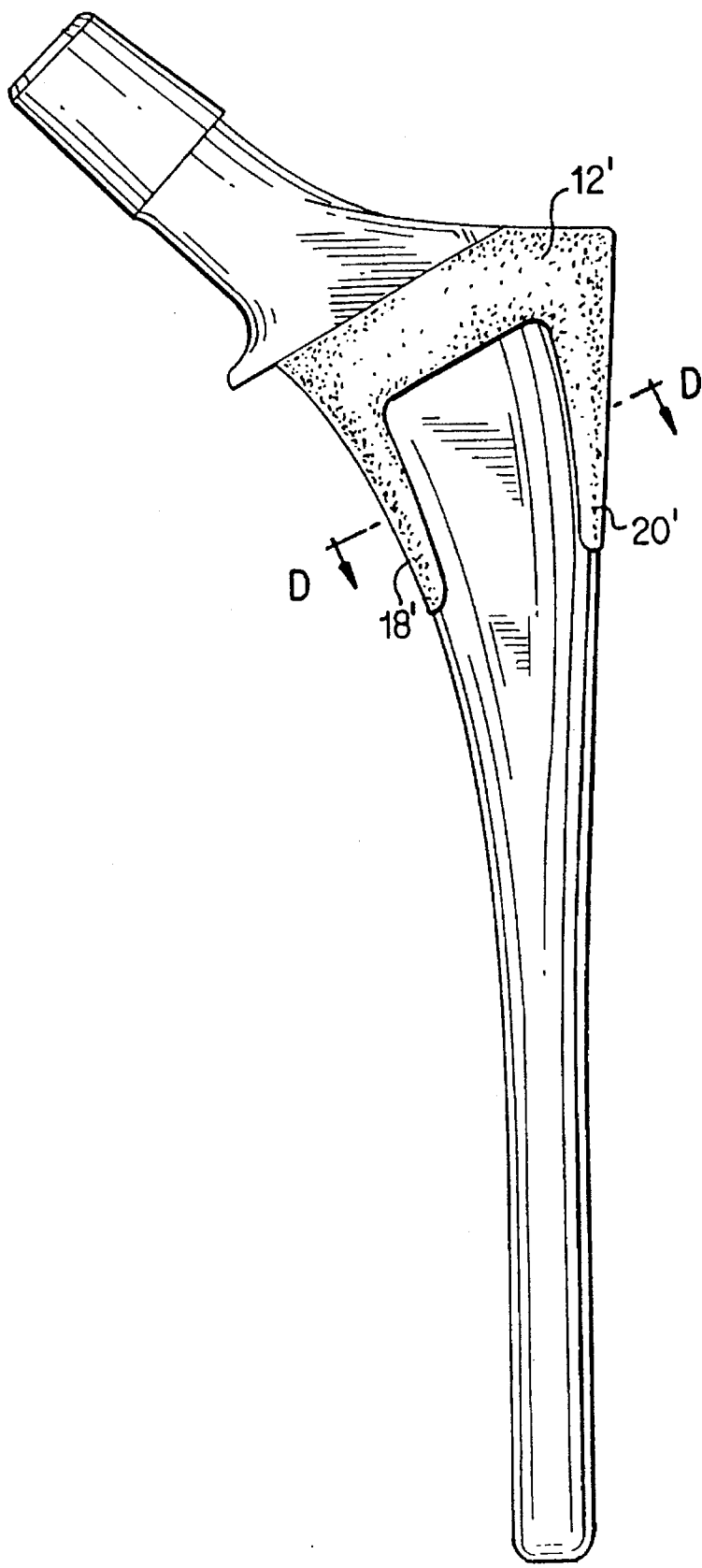
FIG. 6 is a side view of an alternative spacer attached to the prosthesis.
Figure 7:
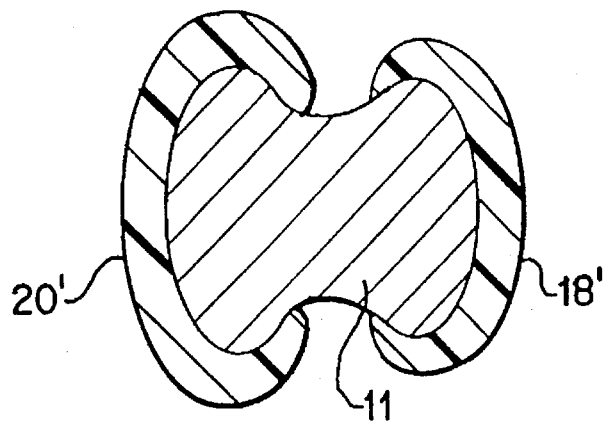
FIG. 7 is a cross-sectional view of the prosthesis through line D—D in FIG. 6.

FIGS. 6 and 7 illustrate an alternative embodiment in which only two extending legs are utilized. According to this alternative embodiment, Spacer 12 is provided with only two distally extending legs: medial leg 18' and lateral leg 20'. FIG. 7 shows how the two distally extending legs 18', 20' of the alternative embodiment encompass the prosthesis. Spacer 12' is otherwise substantially the same as spacer 12.

Figure 10:
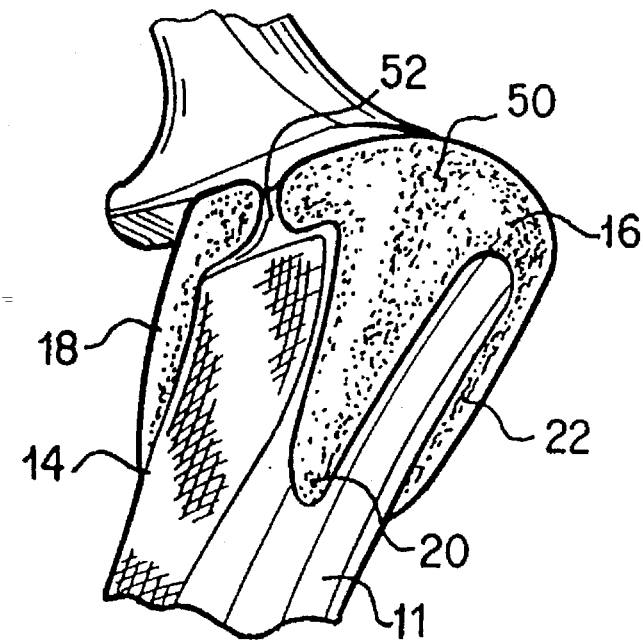
FIG. 10 is a perspective view of a further alternative embodiment of the present invention.
Figure 9:
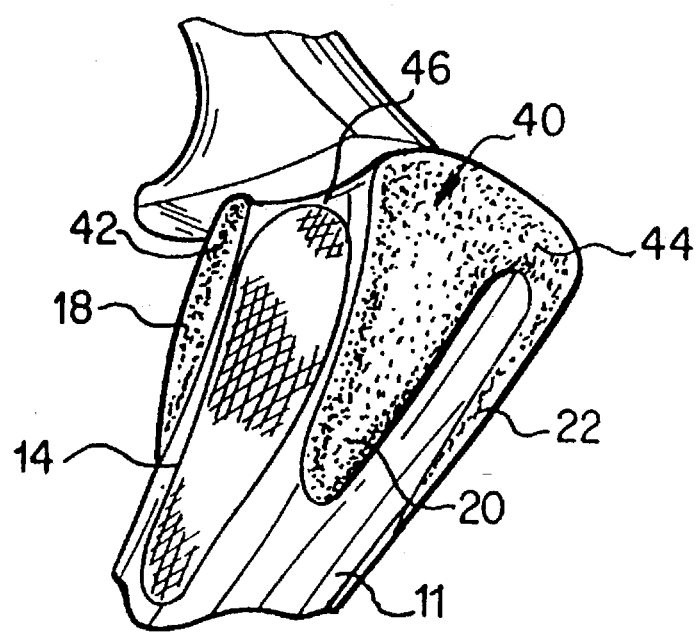
FIG. 9 is a perspective view of another alternative embodiment of the prosthesis according to the invention.

Alternative structures also include designs that do not have a continuous ring around the upper portion of the spacer (FIG. 9) or are otherwise provided with vent holes or means to prevent or control pressurization of the bone cement in the canal when the prosthesis is inserted (FIG. 10). Spacer 40, shown in FIG. 9, has a medial portion 42 which is completely separate from lateral portion 44. Medial leg 18, as previously described, is within medial portion 42 and, similarly, lateral legs 20, 22 are in lateral portion 44. Gap 46 between portions 42 and 44 prevents pressurization, while legs 18, 20 and 22 ensure proper centralization. Spacer 50, shown in FIG. 9, has vents 52 formed in circumferential portion 16 along the posterior and anterior sides to prevent or control pressurization. The size of vents 52 can be changed to vary the amount of pressurization of the bone cement as the prosthesis is inserted into the bone canal by controlling the amount of bone cement that is allowed out. Again, legs 18, 20 and 22 ensure proper centralization. These embodiments for reducing or eliminating pressurization also may be employed with a two-legged spacer as shown in FIG. 6.

In each of the embodiments, the spacer is preferably injection molded directly onto the base element, to provide an integral, single piece prosthesis for implantation and to ensure a strong bond between the base element and the spacer. The manufacturing process involves preparing the base element for the molding, and then molding the spacer thereon. To prepare the base element for molding, it is subjected to a gas plasma cleaning process. Preferably, a Gas Plasma Unit Model C-24 from Advanced Plasma Systems, Inc. is utilized. The gas plasma unit applies an ionized mixture of oxygen and argon gases (40% $O_2$ and 60% Ar) to the prosthesis, which provides a clean, active, oxidized surface that is extremely wettable and allows the molded material to adhere to the prosthesis easily.

In use of the gas plasma unit, the prosthesis is placed on a fixture to hold the element, and placed in a chamber. The chamber is then closed, and evacuated to 225 millitorr. The gas mixture of 40% $O_2$ and 60% Ar is then added. The plasma field is energized by a 950 watt R.F. Fresh gases are circulated through the chamber at a rate of 0.5 S.L.M. After twenty minutes of R.F., the chamber is purged with nitrogen gas.

The prosthesis and the supporting fixture is then placed in an induction heater and preheated to about 500° F.±50° F., and then placed directly into the mold, such that the prosthesis does not drop significantly in temperature. Preheating the prosthesis before the molding step enhances the cement to substrate transition at the critical end points of the molded geometry. The raised temperature of the prosthesis provides a neutral environment for the PMMA attachment and for uniform cooling of the prosthesis and spacer.

The spacer is preferably molded from commercial grade PMMA powder blended with 7% by weight $BaSO_4$ powder that has been extruded into pellets. The mold itself is modular to fit all stem sizes. The outer portion of the mold is made of stainless steel, and the inner portion is a flexible elastomeric liner that prevents the prosthesis from being scratched or deformed and allows spacers of different dimensions to be molded under high pressure. In the molding process, the raw material is loaded into a sealed hopper, and the mold is preheated to 120° F.±10° F. The preheated prosthesis is placed into the preheated mold cavity, and the mold is closed and the molding cycle begins. The initial pressure is built up to 1500 psi, and the mold is filled to a certain volume with the raw material. The pressure is reduced to 250 psi until the complete fill of the mold is achieved. The pressure is held until the mold cavity pressure starts to decrease. The pressure drops to zero, and the clamp pressure is maintained until the part solidifies, and the prosthesis can be ejected. The prosthesis is then trimmed as necessary with a hot knife.

For final finishing, the prosthesis is inspected visually using X-rays, and sterilized with gamma irradiation. The prosthesis is then additionally heated to 120° F. for 24 hours.

As an alternative, molding can be accomplished at lower temperature and pressure by first mixing the bone cement powder with a curing agent and injecting the liquid bone cement into the mold to harden.

We claim:

1. A prosthesis with an integral proximal spacer, comprising:

an elongated base element configured and dimensioned for insertion into the femoral bone canal with a proximal end and a distal end and having medial, lateral, anterior, and posterior surfaces, wherein said base element defines a plurality of depressions therein adjacent the proximal end on any of said surfaces; and a polymeric spacer member secured to said base element with a circumferential portion surrounding the proximal end of said base element, said spacer member further having a medial leg and at least one lateral leg, each leg extending distally along the base element and having protrusions extending into said depressions, said legs tapering to a reduced thickness and width in the distal direction.

2. The prosthesis of claim 1, wherein said at least one lateral leg comprises a first leg extending distally along a lateral-anterior surface of the base element located along an area joining the lateral surface and the anterior surface, and a second leg extending distally along a lateral-posterior surface of the base element located along an area joining the lateral surface and the posterior surface, each said leg terminating at a distal end separate from adjacent legs.

3. A prosthesis with an integral proximal spacer, comprising:

an elongated base element configured and dimensioned for insertion into the femoral bone canal with a proximal end and a distal end, and having medial lateral, anterior, and posterior surfaces, wherein said base element defines a plurality of depressions therein adjacent the proximal end on any of said surfaces; and a spacer member secured to said base element with a circumferential portion surrounding the proximal end of said base element, said spacer member further having a medial leg and at least one lateral leg, each leg extending distally along the base element and having protrusions extending into said depressions, said legs tapering to a reduced thickness and width in the distal direction, and wherein said at least one lateral leg comprises a first leg extending distally along a lateral-anterior surface of the base element located along an area joining the lateral surface and the anterior surface, and a second leg extending distally along a lateral-posterior surface of the base element located along an area joining the lateral surface and the posterior surface, each said leg terminating at a distal end separate from adjacent legs, and wherein said circumferential portion has a tapered distal edge to facilitate insertion into the bone canal.

4. The prosthesis of claim 3, wherein said tapered distal edge is tapered and feathered to provide substantially no discontinuity between said base element and spacer member along said edge.

5. A prosthesis implantation kit, comprising the prosthesis of claim 1 in combination with a femoral bone canal reamer, wherein said circumferential portion of the prosthesis spacer member defines an outer profile shaped to match a reamed femoral canal and said reamer defines an outer reaming profile configured and dimensioned to ream the femoral bone canal to substantially match said circumferential portion outer profile for sealing contact between the bone canal and spacer member such that bone cement deposited in the canal is pressurized when the prosthesis is inserted therein and seated against the reamed canal.

* * * * *

UNITED STATES PATENT AND TRADEMARK OFFICE
CERTIFICATE OF CORRECTION

PATENT NO. : 5,549,705
DATED : August 27, 1996
INVENTOR(S) : Michielli, et al.

It is certified that error appears in the above-identified patent and that said Letters Patent is hereby corrected as shown below:

Title page,
Item [62], "Division of Ser. No. 234,485, Apr. 28, 1994, Pat. No. 5,507,832" should be changed to "Division of Ser. No. 234,485, Apr. 28,1994, Pat. No. 5,507,832, which is a continuation-in-part of Ser. No. 18,452, Feb. 14, 1994, abandoned, which is a continuation of Ser. No. 14,589, Oct. 26, 1993, abandoned."

Column 1,
Lines 4-5, "This is a division, of Ser. No. 08/234,485 filed Apr. 28, 1994 now U.S. Pat. No. 5,507,832" should read -- This is a division of Ser. No. 08/234,485, filed Apr. 28, 1994, now U.S. Pat No. 5,507,832, which is a continuation-in-part of application Ser. No. 29/018,452, filed Feb. 14, 1994, now abandoned, which is a continuation of application Ser. No. 29/014,589, filed Oct. 26, 1993, now abandoned. --.

Signed and Sealed this

Sixth Day of November, 2001

Attest:

*Attesting Officer*

NICHOLAS P. GODICI
*Acting Director of the United States Patent and Trademark Office*